United States Patent [19]

Kent

[11] 4,237,723
[45] Dec. 9, 1980

[54] CONTROL MEANS FOR A PIPE TESTER
[75] Inventor: Francis J. Kent, Wallingford, Pa.
[73] Assignee: Wean United, Inc., Pittsburgh, Pa.
[21] Appl. No.: 737,644
[22] Filed: Nov. 1, 1976
[51] Int. Cl.³ .................. G01M 19/00; G01N 3/10
[52] U.S. Cl. .................................... 73/49.6
[58] Field of Search ............................ 73/49.5, 49.6
[56] References Cited

U.S. PATENT DOCUMENTS

| | | | |
|---|---|---|---|
| 2,050,629 | 8/1936 | Quereau et al. | 73/735 |
| 2,705,888 | 4/1955 | Sedgwick | 73/49.6 |
| 2,907,202 | 10/1959 | McConnell | 73/49.6 |
| 3,312,103 | 4/1967 | Goeke | 73/49.6 |
| 3,350,921 | 11/1967 | Braver et al. | 73/49.6 |

FOREIGN PATENT DOCUMENTS 1091243 11/1967 United Kingdom ................ 73/49.6

*Primary Examiner*—S. Clement Swisher
*Attorney, Agent, or Firm*—Daniel Patch; Suzanne Kikel

[57] ABSTRACT

A transducer control arrangement in a hydrostatic pipe testing machine or pipe tester, for preventing a change in the positioning of the pipe relative to a testhead seal as testing fluid is introduced into the pipe. A transducer signal activates at least one pump to operate a piston cylinder assembly connected to the testhead to reduce or eliminate any relative movement between the testhead seal and the pipe.

4 Claims, 4 Drawing Figures

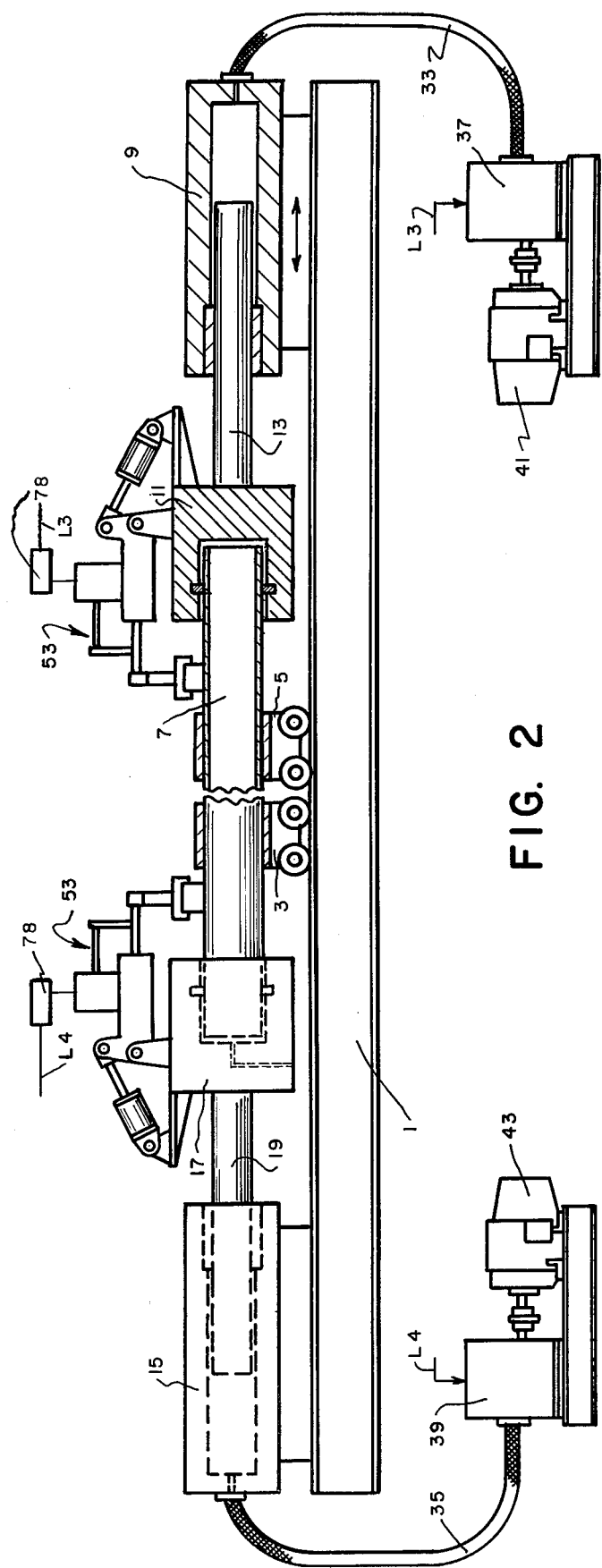

CONTROL MEANS FOR A PIPE TESTER

The present invention pertains to maintaining the relative position of the pipe ends within the testheads of a pipe tester.

In present day practice, a pipe is tested for mechanical strength and fluid tightness, or its diameter is expanded to improve its physical properties by placing the pipe between two testheads, of which at least one moves inwardly toward the pipe so as to seal the pipe at or near its ends, and introducing pressurized fluid, such as water, into the interior of the pipe.

When the pressure of the fluid reaches a significant value, pressure build up in the pipe causes the testheads, and hence their seals, to move away from the ends of the pipe. One reason for this is that the radial expansion of the pipe shortens the pipe. This condition causes the seals, which may take the form of sealing rings or sealing plates, arranged in the testheads to be subject to the movement of the pipe, thereby breaking the sealing relationship of the plates and causing a loss in pressure, or causing wear of the sealing rings.

Several pipe testers have attempted to compensate for this objectionable relative movement; for instance, U.S. Pat. Nos. 2,671,339; 2,707,876; and 2,725,743. In these designs, the effectiveness of the compensating mechanism demands that proper adjustments and/or exchanging of parts be made to the pipe testers. In U.S. Pat. Nos. 2,671,339 and 2,725,743 patents, for varying diameter pipes, varying diameter rams have to be installed in the testheads. In U.S. Pat. No. 2,707,876 patent the gripper inserts have to be replaced each time a different diameter pipe is to be tested. U.S. Pat. No. 2,725,743 involves a complicated, closed hydraulic system, which lessens its efficiency due to inherent pressure losses. All three designs greatly complicate the construction of the testheads and makes the testhead more expensive.

It is therefore, an object of the present invention to overcome the above disadvantages existing in pipe testing machines by providing a simpler, more economical, and more efficient means for compensating for the objectionable relative movement between the seal and the pipe, which allows a simpler testhead construction and for which the opposed testheads, along with their means for moving them, can be made of a substantial, identical construction.

In particular, a still further object of the present invention is to provide: a pair of opposed testheads, each having apertures for receiving a different end of the pipe when arranged between the testheads; a sealing element arranged in each aperture, means for moving at least one of the testheads axially of the arranged pipe to establish a sealing of the different ends of the pipe with a different one of the sealing elements; means associated with one of said testheads for introducing testing fluid under pressure into the interior of the arranged pipe; transducer control means for producing a control signal representative of a condition, which condition is capable of changing or actually does change a datum position of at least one of the sealing elements and an associated end of the arranged pipe upon the introduction of testing fluid therein; the compensating means responsive to the control signal for operating the means for moving at least one of said testheads, thereby eliminating or counteracting any movement between the sealing elements and the ends of the pipe to maintain the datum position between the sealing elements and the pipe.

And, yet a still further object of the present invention is to provide for the transducer control means either a pressure transducer or a position transducer, in combination with other control elements.

These objects, as well as other features and advantages of the present invention, will be better understood and appreciated when following description of two embodiments thereof is read along with the accompanying drawings of which:

FIG. 2 is an elevational view, partly in section, illustrating a second embodiment of the present invention;

FIG. 3 is a detailed, enlarged partial view of the second embodiment of the present invention showing the tailstock testhead; and FIG. 4 is a broken away, sectional view of a seal arranged in a testhead, shown in the earlier FIGURES.

Figure 1:
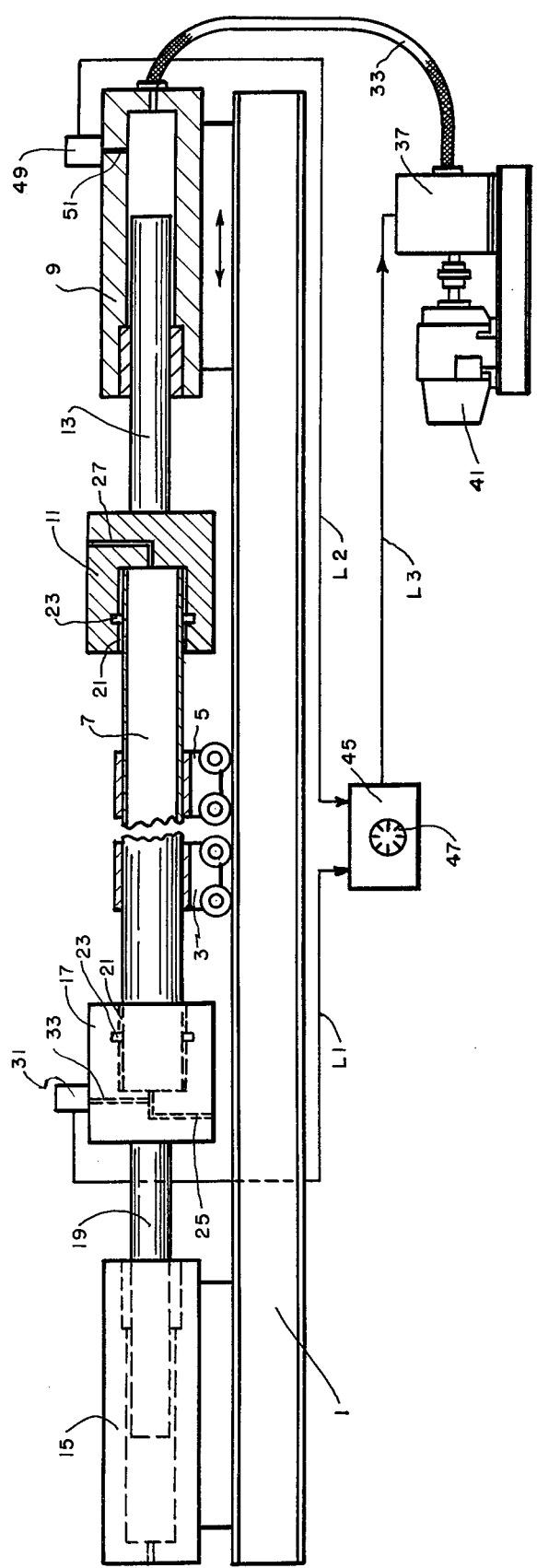
FIG. 1 is an elevational view, partly in section, illustrating the first embodiment of the present invention.

Referring first to FIG. 1, there is shown a diagrammatical arrangement for a pipe testing machine, into which a pipe has already been positioned. On a frame 1 rests two moveable clamps 3 and 5 for supporting the pipe 7, which is broken away for simplicity. To the right of frame 1, as one views this FIG. 1, and secured thereto is a single acting tailstock cylinder 9 to which a tailstock testhead 11 is connected by ram 13 of the cylinder 9; and to the left of frame 1 is mounted a single acting headstock cylinder 15 with headstock testhead 17 connected to the headstock cylinder by ram 19. An aperture 21 in each of testheads 11 and 17 receives a different end of the pipe 7 which ends contact the walls of the testhead. A gasket or seal 23 encircles the outer periphery of the pipe ends, and is anchored in testheads 11 and 17. As testing fluid, or water, is introduced into the interior of the pipe through space 25 in headstock testhead 17, air is vented through line or space 27 in tailstock testhead 11. When the air has been expelled from the pipe, the venting valve (not shown) is closed and the required testing pressure of 10,000 p.s.i., for example, can be established in the pipe.

The desired amount of pressurized water is locked into the pipe by a decompression valve, connected to an hydraulic intensifier system (not shown). As the water enters the pipe, the pressure is detected by a pressure transducer 31 situated over a connection or space 33 which extends down into space 25 of the testhead 17. Rams 13 and 19, and therefore, headstock and tailstock cylinders 9 and 15, respectively, are brought into an initial locking or testing position and retracted after testing of the pipe by a main hydraulic system. The operation and construction of the main hydraulic system, the locking mechanism, the hydraulic intensifier and the auxiliary motors for returning the testheads to a neutral condition when the pressure subsides may be similar to that shown and described in U.S. Pat. Nos. 2,671,339; 2,707,876; and 2,725,743. Since an understanding of these elements is not necessary for an understanding of the present invention, these elements have been deleted from the description and FIGURES of the present invention for clarity.

After the pipe is arranged in the testheads, the pressure in both cylinder assemblies 9 and 15 is blocked via the main hydraulic system to hold testheads 11 and 17 stationary for testing. At the back of tailstock cylinder 9 is an hydraulic line 33 which is not part of the main hydraulic system connected to a reversible pump 37, which receives fluid from a servo valve (not shown) and which is driven by a motor 41. The pressure is increased or decreased in piston cylinder assembly 9 by pump 37, in which case, the moving piston acts to move the pipe so there will be no relative movement between the seals or gaskets 23 and the ends of the pipe.

From transducer 31 runs an electrical line $L_1$ to a comparator 45, which establishes a pressure ratio by dial 47, more about which will be explained in the operation of the invention. At the top right of comparator 45 is another electrical line $L_2$, extending to another pressure transducer 49, mounted on tailstock cylinder 9, and connected by space 51 to the interior of tailstock cylinder to detect pressure in the tailstock cylinder. At one side of comparator 45 is electrical line $L_3$, which is connected to pump 37. Pressure transducers 31 and 49 may be of the type produced, for instance, by BLH Electronics or Standard Controls.

As mentioned, FIGS. 2 and 3 illustrate another embodiment of the present invention, which embodiment eliminates the two pressure transducers 31 and 49, the comparator 45, and the electrical connections $L_1$ and $L_2$. In this embodiment the lines $L_3$ and $L_4$ are associated with the pump controls instead of the comparator 45 and this embodiment employs pump unit elements 35, 39 and 43 connected to headstock cylinder 15. Instead of the pressure transducers, there are provided for each testhead position transducers. In FIG. 2, testheads 11 and 17 are again illustrated in which the steel pipe 7 achieves a sealing relationship with the testheads, carried by rams 13 and 19 by being received in apertures 21, which anchor gaskets 23 engaging the outer diameter of the pipe. In order for this embodiment to function properly the pipe ends are allowed to move relative to the seals and therefore are slightly spaced away from the wall of testheads. Mounted on testheads 11 and 17 is a transducer arrangement 53 which is shown in detail in FIG. 3. Transducer arrangement 53 senses any axial movement between the pipe and testhead as the testing fluid enters the interior of the pipe and pressure builds up to cause the pipe to move away from the testheads. Sensing arrangement 53 comprises a linear variable differential transducer (LVDT) 55 sometimes referred to as a transformer, supported by a spring centering device 57, which is hinged on testhead 11 by a fulcrum 59, and has a bracket 61 pivotally connected to a clevis 63 of a piston rod 65 of a pneumatic or hydraulic cylinder 67, mounted on shelf 69, extending from the top of the testhead. Core rod 71 of LVDT 55 is mounted for movement with rod 73 of spring centering device 57, which rod 73 carries a permanent magnet 75. As the sensing arrangement 53 is raised and lowered by cylinder 67, magnet 75 is pulled away from or attracted to pipe 7.

Even though FIG. 3 shows one such arrangement, 53, it can be seen in FIG. 2 that another such arrangement exists on testhead 17.

LVDT 55 is wired to an amplifier 77, which is electrically connected to a pump control 78, and which, in turn, controls the operation of pump units 37 and 39 associated with tailstock cylinder 9 and headstock cylinder 15, respectively. LVDT 55 may be, for instance, Model 24DCDT-1000, sold by Sanborn Division of Hewlett Packard Corp., Waltham, Mass.

FIG. 4 is an exaggerated view showing the deformation of the seal or gasket 23 in testheads 11 or 17, as the pipe tends to move away from the testheads, and applies only to the second embodiment.

A brief explanation of the operation of the embodiment in FIG. 1 will be given first. Pipe 7 is advanced onto the frame 1 by a loading device, which is not shown in the FIGURES, and is positioned between testheads 11 and 17 where it is supported by movable clamps 3 and 5. Testheads 11 and 17 are moved inwardly toward each other by oil entering both tailstock and headstock cylinders 9 and 15, from the main hydraulic system (not shown).

As mentioned, the operation and design of the present invention is similar to well known present day pipe testing practice in that headstock testhead 17 is mounted stationarily and tailstock testhead 11 is adjustable. The operator of the pipe tester admits enough oil into the cylinders to obtain a sealing relationship between the ends of the pipe and gaskets 23 of testheads 11 and 17. Once this relationship is established, the oil is blocked in cylinders 9 and 15. It is to be noted that various types of seals may be employed such as a round plate seal contacting the open ends of the pipe; a seal in the interior of the pipe; or a seal around the outer periphery of the pipe, as illustrated herein.

Before testing fluid is introduced into the interior of the pipe through space 25 in testhead 17, or before a nominal amount of water fills the pipe, the dial 47 on comparator 45 is set to the proper pressure ratio between the cylinder pressure and the testing pressure for a particular pipe to be tested under a desired pressure. The ratio is determined by the operator and in actual practice, may represent a difference of 500 lbs., i.e., each cylinder pressure will be 500 lbs. greater than the test pressure for a given pipe size and sufficient to allow compensation to be affected according to the teaching of this invention.

As water first enters the pipe, both pressure transducers 31 and 49 read zero pressure, but as water creates pressure, pressure transducer 31 senses the pressure and sends by electrical line $L_1$ a representative signal to comparator 45. Concurrently, pressure transducer 49 senses the compressive reactionary pressure in tailstock cylinder 9, and sends by electrical line $L_2$ a representative signal to comparator 45. The comparator 45 being set to a particular pressure ratio will send a signal over line $L_3$ to pump 37 to control the amount of fluid being supplied through line 33 to tailstock cylinder 9, which amount is proportionately, and as noted, always slightly greater than that required to balance the testing pressure to keep testheads 11 and 17 in the desired position. From this, it can be seen that little, if any, relative movement will occur between testheads 11 and 17 and the ends of the pipe, and more importantly, between the gaskets 23 and the pipe. As the test pressure continues to build up in the pipe, both transducers 31 and 49, in association with comparator 45 and pump 37 will continue to deliver oil to cylinder 9 at a pressure to maintain the seals in their proper relationship until the pressure in the pipe reaches its maximum testing value.

Once the desired testing pressure is established, it will be maintained automatically for the required testing period. Subsequently, while pressure is gradually being released in the pipe as the water exits, pressure in cylinder 9 decreases proportionately through the operation of the pressure transducers 31 and 49 sending signals to comparator 45, which sends corresponding signals to pump 37 to meter the oil out of the cylinder 9, and doing so at the established ratio setting. When the nominal amount of pressure is reached, transducers 31 and 49 discontinue to function, the testheads move away from the ends of the pipe, and the water is emptied from the pipe.

The embodiment in FIG. 2 operates with two sensing arrangements 53 on the testheads 11 and 17 of cylinders 9 and 15, in which the pumps 37 and 39 are controlled by control unit 78 of each sensing arrangement 53. In explaining this operation and without repeating the above steps, let us begin at the time when the pipe is positioned between testing head 11 and 17. Oil from the main hydraulic system is pumped into cylinders 9 and 15 so that apertures 21 can receive the ends of the pipe without the ends contacting the interior walls of the testheads. At this point, sensing arrangement 53 has been raised away from the feeding level of the pipe by piston cylinder assembly 67. Once the sealing relationship is established in the usual testing fashion, piston cylinder assembly 67 is operated to lower sensing arrangement 53 so that magnet 75 contacts the top outer surface of the pipe. Once the nominal amount of water enters the pipe and the pressure builds up to cause the pipe to move away from testheads 11 and 17, it can be seen that spring centering device 57 allows magnet 75 to remain in contact with the pipe. However, if any axial movement occurs, core rod 71 of LVDT 55 is displaced, causing LVDT 55 to send a representative signal of this movement to the amplifier 77, which, in turn, sends a signal to the control unit 78. Pump 37 then operates to deliver a sufficient amount of oil under pressure to cylinder 9. LVDT 55 reacts to movements of less than 0.001 inches, and is capable of controlling the pump so as to restore the original condition before any drastic movement between gasket 23 and the pipe even occurs. In this regard, FIG. 4 depicts the relative movement between the seal and pipe before the correction is made. This corrective action continues during the pressure build-up period and continues during the pressure release period, during which pump 37 remains under the control of LVDT 55. The same action occurs at the headstock end where pump 39, under the control of another LVDT 55 and unit 78, delivers oil into or meters out of cylinder 15. From the above, it is obvious that the invention maintains the desired sealing condition. From the above description and operation of the present invention, it is easy to understand that the testheads are similar in construction and operation, and with some modifications can operate as either a tailstock or headstock testhead.

In accordance with the patent statutes, I have explained the principles and operation of my invention, and have illustrated and described what I consider to represent the best embodiment thereof.

I claim:

1. An hydrostatic pipe testing apparatus comprising a pair of opposed testheads each having an aperture for receiving a different end of a pipe when the pipe is arranged between said testheads,
    a sealing element arranged in each of said apertures which have an end wall,
    separate means for moving said testheads axially of the arranged pipe to position said sealing element around or inside an associated end of the pipe in a manner to establish a datum position for each said sealing element and for positioning the pipe slightly away from said end wall of said each aperture receiving said different end of the pipe,
    means associated with one of said testheads for introducing testing fluid under pressure into the interior of the arranged pipe,
    an electrical linear variable differential transducer means mounted on each said opposed testheads, each arranged to be associated with an opposite end portion of the pipe external of said respective testhead for sensing a displacement of an associated sealing element relative to its datum position and for producing separate electrical signals representative of said displacements,
    separate means for mounting each said transducer means on an associated testhead for movement therewith including means for selectively bringing said transducer means into a sensing position with an end portion of the pipe, and into a non-sensing position away from an end portion of the pipe, whereby the pipe may be brought to and from the testing apparatus, and
    compensating means associated with each said testhead for receiving and responding to said electrical signals of said respective transducer means for effecting separate operation of said means for moving said testhead in the direction to counteract said displacement of said end of the pipe to maintain said sealing elements in said datum positions.

2. An hydrostatic pipe testing apparatus according to claim 1, wherein said linear variable differential transformer means includes:
    means for adhering to an outer surface of the pipe, and
    resilient means for supporting said adhering means for continually urging said linear variable differential transformer means to said inoperative position.

3. An hydrostatic pipe testing apparatus according to claim 1, wherein said means for positioning said linear variable differential transformer means includes:
    a piston cylinder assembly mounted on said test heads for pivoting said linear variable differential transformer means.

4. An hydrostatic pipe testing apparatus according to claim 2, wherein said adhering means includes a permanent magnet.

* * * * *